(12) United States Patent
Romo et al.

(10) Patent No.: US 12,642,681 B1
(45) Date of Patent: *Jun. 2, 2026

(54) BACK BRACE WITH HEIGHT ADJUSTABLE RIGID PANEL

(71) Applicant: Aspen Medical Products, LLC, Irvine, CA (US)

(72) Inventors: Albert V. Romo, Lakewood, CA (US); Geoffrey Wong, Costa Mesa, CA (US); Jane Price, Anaheim, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/049,700

(22) Filed: Feb. 10, 2025

Related U.S. Application Data

(63) Continuation of application No. 17/687,574, filed on Mar. 4, 2022, now Pat. No. 12,220,339.

(60) Provisional application No. 63/157,590, filed on Mar. 5, 2021.

(51) Int. Cl.
*A61F 5/02* (2006.01)

(52) U.S. Cl.
CPC ................................... *A61F 5/024* (2013.01)

(58) Field of Classification Search
CPC .... A61F 5/01; A61F 5/02; A61F 5/022; A61F 5/024; A61F 5/026; A61F 5/028; A61F 5/03; A61F 5/04; A61F 5/05; A61F 5/05808; A61F 5/24–28; A61F 5/30; A61F 5/37; A61F 5/042–055; A61F 5/0123; A61F 5/0125; A61F 5/0585; A61F 2005/0167; A61F 2005/0188
See application file for complete search history.

(56) References Cited

U.S. PATENT DOCUMENTS

| | | | |
|---|---|---|---|
| 4,475,543 | A | 10/1984 | Brooks et al. |
| 5,499,965 | A | 3/1996 | Sanchez |
| 9,636,247 | B2 | 5/2017 | Miller et al. |
| 12,138,192 | B1 | 11/2024 | Romo |
| 2004/0220503 | A1 | 11/2004 | Kozersky |
| 2008/0045873 | A1 | 2/2008 | Zours |

(Continued)

FOREIGN PATENT DOCUMENTS

| | | |
|---|---|---|
| DE | 202017001198 U1 | 1/2018 |
| WO | 2007027573 A2 | 3/2007 |
| WO | 2022187723 A1 | 9/2022 |

OTHER PUBLICATIONS

EP22764208.9 filed May 10, 2023 Extended European Search Report dated Apr. 9, 2025.

(Continued)

*Primary Examiner* — Alireza Nia
*Assistant Examiner* — Andrew Jun-Wai Mok
(74) *Attorney, Agent, or Firm* — Rutan & Tucker, LLP

(57) ABSTRACT

A height adjustable orthosis is described. The orthosis features a belt and a posterior frame. Coupled to the belt, the posterior frame includes a first panel including at least a first fastener and a second rear panel including at least a first lock member and a second locking member. The first panel and the second panel are configured to move vertically relative to each other to position the first fastener to engage at least (1) the first locking member at a first height or (2) the second locking member as a second height.

19 Claims, 6 Drawing Sheets

(56) References Cited

U.S. PATENT DOCUMENTS

| | | | |
|---|---|---|---|
| 2008/0262401 A1 | 10/2008 | Wagner et al. | |
| 2009/0045656 A1 | 2/2009 | Chen et al. | |
| 2009/0163841 A1 | 6/2009 | Garth | |
| 2011/0105971 A1 | 5/2011 | Ingimundarson et al. | |
| 2011/0114101 A1 | 5/2011 | Tweardy et al. | |
| 2012/0253251 A1 | 10/2012 | Thornton | |
| 2013/0261521 A1 | 10/2013 | Carter | |
| 2014/0305982 A1 | 10/2014 | Pelland et al. | |
| 2015/0290019 A1 | 10/2015 | Garth et al. | |
| 2016/0081841 A1 | 3/2016 | Miller et al. | |
| 2018/0303699 A1 | 10/2018 | Romo et al. | |
| 2018/0317634 A1 | 11/2018 | Rittenhouse et al. | |
| 2019/0091094 A1 | 3/2019 | Romo et al. | |
| 2020/0103073 A1 | 4/2020 | Lennings et al. | |
| 2020/0179153 A1* | 6/2020 | Wang | A61F 5/028 |
| 2022/0280324 A1 | 9/2022 | Romo et al. | |

OTHER PUBLICATIONS

EP22764208.9 filed May 10, 2023 Partial European Search Report dated Dec. 23, 2024.

PCT/2022/019050 filed Mar. 5, 2022 International Search Report and Written Opinion dated Jun. 1, 2022.

U.S. Appl. No. 17/687,562, filed Mar. 4, 2022 Non-Final Office Action dated Dec. 26, 2023.

U.S. Appl. No. 17/687,562, filed Mar. 4, 2022 Notice of Allowance dated Jun. 7, 2024.

U.S. Appl. No. 17/687,562, filed Mar. 4, 2022 Restriction Requirement dated Jul. 5, 2023.

U.S. Appl. No. 17/687,574, filed Mar. 4, 2022 Non-Final Office Action dated May 7, 2024.

U.S. Appl. No. 17/687,574, filed Mar. 4, 2022 Notice of Allowance dated Sep. 13, 2024.

U.S. Appl. No. 18/942,239, filed Nov. 8, 2024 Non-Final Office Action dated Dec. 29, 2025.

* cited by examiner

BACK BRACE WITH HEIGHT ADJUSTABLE RIGID PANEL

CROSS-REFERENCE TO RELATED APPLICATIONS

This application is a continuation of U.S. patent application Ser. No. 17/687,574, filed Mar. 4, 2022, now U.S. Pat. No. 12,220,339, issued Feb. 11, 2025, which claims the benefit of priority to U.S. Provisional Patent Application No. 63/157,590 filed Mar. 5, 2021, the entire contents of which is incorporated by reference herein.

FIELD

The field of the invention is height adjustable orthoses operating as back braces.

BACKGROUND

The background description includes information that may be useful in understanding aspects of the invention. It is not an admission that any of the information provided herein is prior art or relevant to the presently claimed invention, or that any publication specifically or implicitly referenced is prior art.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Back braces are often used by users for support. Currently, back braces are manufactured and distributed by taking into account governmental coding and reimbursement procedures that encourage off-the-shelf products with minimal skews and products that target a large number of patients. At this time, governmental coding and reimbursement procedures encourage back braces to be sized to accommodate an "average-sized" male (e.g., approximately seventy-fifth ($75^{th}$) percentile male). While posterior panels of the brace braces are sized to properly fit an average sized male, there are many patients for whom the back brace is improperly sized due to their less common physical characteristics, such as petite (5'3" and under) or a tall (6'4" and over) patients, patients with extremely long or short torsos, or the like. An adjustable back brace will enable an orthopedic brace manufacturer to fully comply with governmental procedures for coding and reimbursement, while at the same time, provide a better-fitting orthosis.

Hence, it would be desirable for orthoses to have mechanisms that can alter their fit in order to accommodate the physical characteristics of the patient.

DETAILED DESCRIPTION

Figure 1:
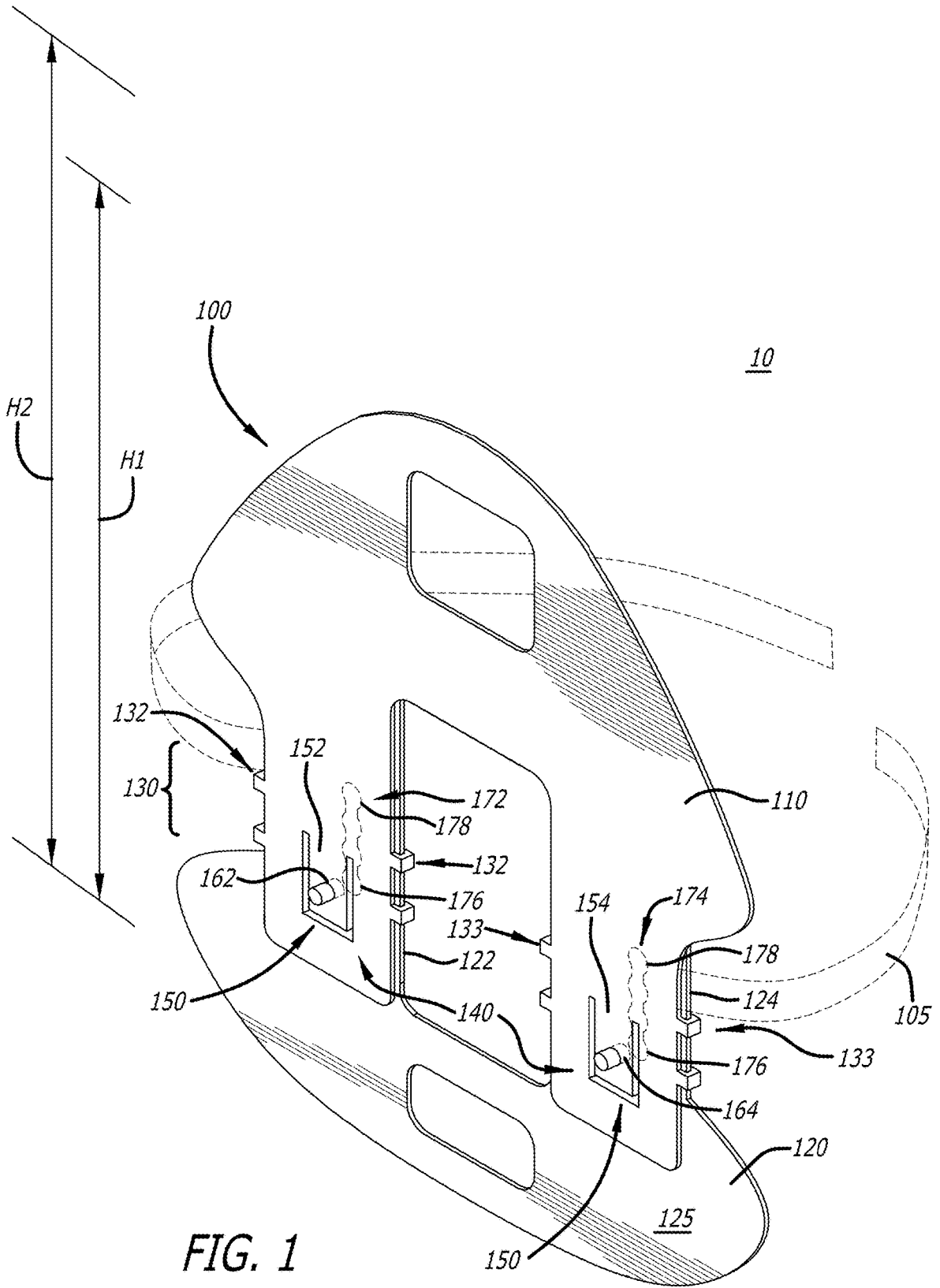
FIG. 1 is a perspective view of a first exemplary embodiment of an orthosis featuring a multi-panel, adjustable posterior frame with height adjustment fasteners.

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

A size (e.g., height and/or width) adjustable orthosis (e.g., back brace) is contemplated. For instance, a height adjustable orthosis may be configured with a posterior frame and a belt coupled to the posterior frame. The posterior frame features a first (rear) panel and a second (rear) panel, where the first panel partially overlays and is slidably engaged with the second panel. According to a first embodiment of the disclosure, the first panel features a first set of fasteners and the second panel features a plurality of locking members, including at least a first set of locking members and a second set of locking members. Herein, the "set of fasteners" constitutes one or more fasteners while each of the "first set of locking members" and the "second set of locking members" constitutes one or more locking members configured and sized for coupling to the corresponding set of fasteners. For embodiments described herein, the first and second panels are configured to move vertically relative to each other, and once set to a desired, collective height, the set of fasteners is set to engage with (1) the first set of locking members when a first height position is selected or (2) the second set of locking members when a second height position is selected.

It is contemplated that each fastener may include, but is not limited or restricted to a flexible tab, a lock screw, a latch, or any other fastening device. For example, a flexible tab may be configured with a protrusion for insertion into a selected locking member being one of the first set of locking members or the second set of locking members. For this embodiment, each of the first set of locking members and the second set of locking members may be configured as a closed-ended slot sized and dimensioned to receive the protrusion extending from a corresponding flexible tab. Additionally, or in the alternative, one or more of the first and second sets of locking members can be an opening sized and dimensioned to receive the protrusion extending from a corresponding flexible tab.

According to a second embodiment of the disclosure, the first panel is configured with a first set of fasteners and the second panel is configured with a plurality of locking members, including at least the first set of locking members and the second set of locking members. As described below, the first and second panels are configured to move vertically relative to each other, where the set of fasteners is engaged with the first set of locking members at a first height position or is engaged with the second set of locking members at a second height position. However, the operating state of these fasteners is controlled by a fastener adjustment guide.

Herein, the fastener adjustment guide may be configured as a guide wire that is physically coupled to the set of fasteners and configured to place each fastener into a locked state or an unlocked state. More specifically, when placed into a first operating state, the fastener adjustment guide allows each fastener to enter into a locked state. Upon placement into a second operating state, the fastener adjustment guide causes each fastener to enter into an unlocked state. This is accomplished by the fastener adjustment guide recoiling the fastener(s), which causes a protrusion for each fastener located in the first panel to disengage from its corresponding locking member located in the second panel. In response to releasing the fastener adjustment guide to return to its first operating state, each protrusion for the set of fasteners may engage with a corresponding locking member that may be positioned higher on the second panel when the height of the posterior brace is increased or positioned lower on the second panel when the height of the posterior brace is decreased. It is contemplated that, lieu of height adjustments, width adjustments of the orthosis may be conducted in a similar manner as described, where height adjustment is described for the sake of clarity.

I. Height Adjustable Orthosis—First Embodiment

Referring to FIG. 1, a perspective view of a first exemplary embodiment of an orthosis 10 featuring a multi-panel, adjustable posterior frame 100 with height adjustment fasteners 150 is shown. A belt 105 may be attached to the posterior frame 100 to secure the orthosis 10 to the patient. It is contemplated that the belt 105 may correspond to a continuous belt normally positioned behind (outside) the posterior region of the posterior frame 100 or may correspond to a pair of belts attached at different lateral areas of the posterior frame 100. Furthermore, it is contemplated that the belt 105 may correspond to a lumbar sacral orthosis (LSO) style belt that is integrated with the posterior frame 100 to operate as a thoracic LSO (TLSO).

Herein, the posterior frame 100 features a first panel 110, a second panel 120, a panel guide elements 130 (e.g., multiple sets of panel guide elements 132-133), and a fastening mechanism 140. The first panel 110 is positioned posteriorly to the second panel 120, where at least a first set of panel guide elements 132 and a second set of panel guide elements 133 extend from the first panel 110 to engage with and secure the first panel 110 to the second panel 120. These panel guide elements 130 maintain positioning and a slidable connection between the first and second panels 110 and 120. This slidable connection allows the first panel 110 to be adjusted and secured to the second panel 120 using the fastening mechanism 140. This allows for an orthosis with a posterior back panel that is adjustable to the patient's anatomy instead of a predetermined posterior back panel height.

According to one embodiment of the disclosure, the fastening mechanism 140 includes a plurality of height adjustment fasteners 150, which may be deployed as a portion of the first panel 110. For instance, as shown in FIG. 1, the height adjustment fasteners 150 may correspond to flexible lift tabs 152 and 154, where each lift tab 152 and 154 includes a protrusion 162 and 164 for insertion into locking members 172 and 174 formed as a portion of the second panel 120. Additionally, or in the alternative, these locking members 172 and 174 may be segmented into at least a first set of locking members 176 and a second set of locking members 178.

Figures 2A, 2B:
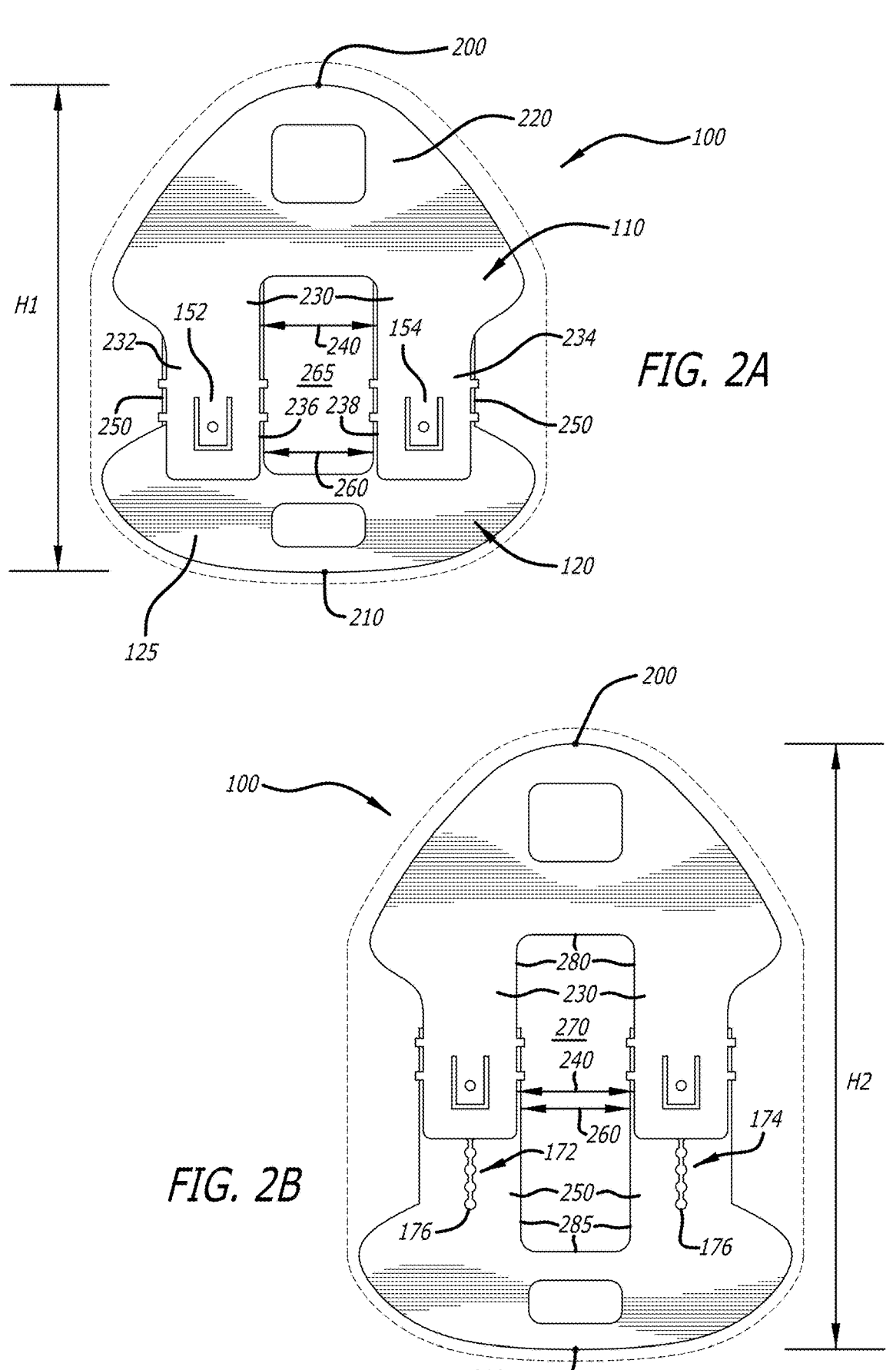
FIG. 2A is a perspective view of the multi-panel, adjustable posterior frame of FIG. 1 positioned in a first state of operation.
FIG. 2B is perspective view of the multi-panel, adjustable posterior frame of FIG. 1 positioned in a second state of operation.

As an illustrative example, the first set of locking members 176 and the second set of locking members 178 may be configured as complementary sets of interlocking apertures formed along columns towards a lower region 125 of the second panel 120. As shown in FIG. 1, the height adjustment fasteners 152/154 can be used to insert or remove protrusions 162/164 from the first set of locking members 176 (interlocking apertures) to the second set of locking members 178 (interlocking apertures) to increase a height of the posterior frame 100 of the orthosis 10, namely increase the collective height of the first and second panels 110 and 120 forming the posterior frame 100 from a first height (H1) to a second height (H2) as also shown in FIGS. 2A-2B. As illustrated by dashed lines, a sleeve (or cover) may be positioned over the posterior frame 100.

The first height (H1) of the posterior frame 100 can be a first vertical distance from an uppermost point of the first panel 110 to a lowermost point of the second panel 120. Additionally, the second height (H2) is a second vertical distance from the uppermost point of the first panel 110 to the lowermost point of the second panel 120 after adjustment of a vertical height of the first panel 110. It is contemplated, as shown in FIG. 1, that the second vertical distance (second height) H2 is greater than the first vertical distance (first height) H1. For example, the second height H2 (e.g., the height created by vertically displaced panels 110 and 120 with height adjustment fasteners 150 inserted into the second set of locking members 178) is greater than the first height H1 (e.g., the height created by panels 110 and 120 with height adjustment fasteners 150 inserted into the first set of locking members 176. It is contemplated that the second vertical distance (H2) is about 15½ inches while the first vertical distance (H1) is about 14 inches.

Referring now to FIG. 2A, a perspective view of the posterior frame 100 of FIG. 1 oriented in a first position is shown. Herein, the height adjustment fasteners 150 are coupled to the first set of locking members 172 (interlocking apertures), where the posterior frame 100 is configured with the first height (H1) denoting a first vertical distance from an uppermost point 200 of the first panel 110 to a lowermost point 210 of the second panel 120. According to this embodiment, the first panel 110 includes an upper area 220 and a first pair of columns 230 extending downward (when worn) from the upper area 220. The upper area 220 is triangular-shaped as this portion of the adjustable posterior frame 100 operates as an upper back support for patients. A spacing 240 is provided between the first pair of columns 230.

One or more height adjustment fasteners 150 (e.g., a first height adjustment fastener 152 and/or a second height adjustment fastener 154) are positioned along posterior surfaces 232 and 234 of the first pair of columns 230. Each of the first height adjustment fastener 152 and/or the second height adjustment fastener 154 includes a protrusion (not shown), which extends anteriorly from these fasteners 152 and 154 and beyond the anterior surfaces 236 and 238 of the first pair of columns 230. These protrusions are sized to engage with any of the locking members 172 and/or 174 such as the first set of locking members 176 and/or the second set of locking members 178 of the second panel 120 as shown in FIG. 1.

As further shown in FIG. 2A, the second panel 120 includes the lower region 125 and a second pair of columns 250 extending upward from the lower region 125 so as to partially overlay, from an anterior perspective, the first pair of columns 230. Each of the second pair of columns 250 (e.g., a first anterior panel column and a second anterior panel column) includes a plurality of locking members vertically oriented and aligned with each other so as to produce the locking members 172 and/or 174. A spacing 260 is present between the second pair of columns 250. As a result, when the second panels 110 and 120 are oriented generally in parallel, the spacings 240 and 260 create a rectangular window 265 to allow clinicians access to a patient's back, which is needed in follow-up visits after back surgery.

Referring to FIG. 2B, a perspective view of the posterior frame 100 forming a portion of the orthosis 10 of FIG. 1 is shown, where the posterior frame 100 is oriented in a second position. Herein, the height adjustment fasteners 152/154 are coupled to the second set of locking members 178 (interlocking apertures) in lieu of the first set of locking members 176 as shown in FIG. 2A. As a result, the posterior frame 100 is configured with the second height (H2) denoting a second vertical distance from the uppermost point 200 of the first panel 110 to the lowermost point 210 of the second panel 120. The second height (H2) is greater than the first height (H1) by a distance measured between the first set of locking members 176 and the second set of locking members 178. Collectively, a rectangular window 270, formed by the spacings 240 and 260 and bounded by inner edges 280 associated with the first pair of columns 230 and inner edges 285 associated with the second pair of columns 250, is larger in size than the rectangular window 265 when the posterior frame 100 is oriented in the first position as illustrated in FIG. 2A.

Figure 3:
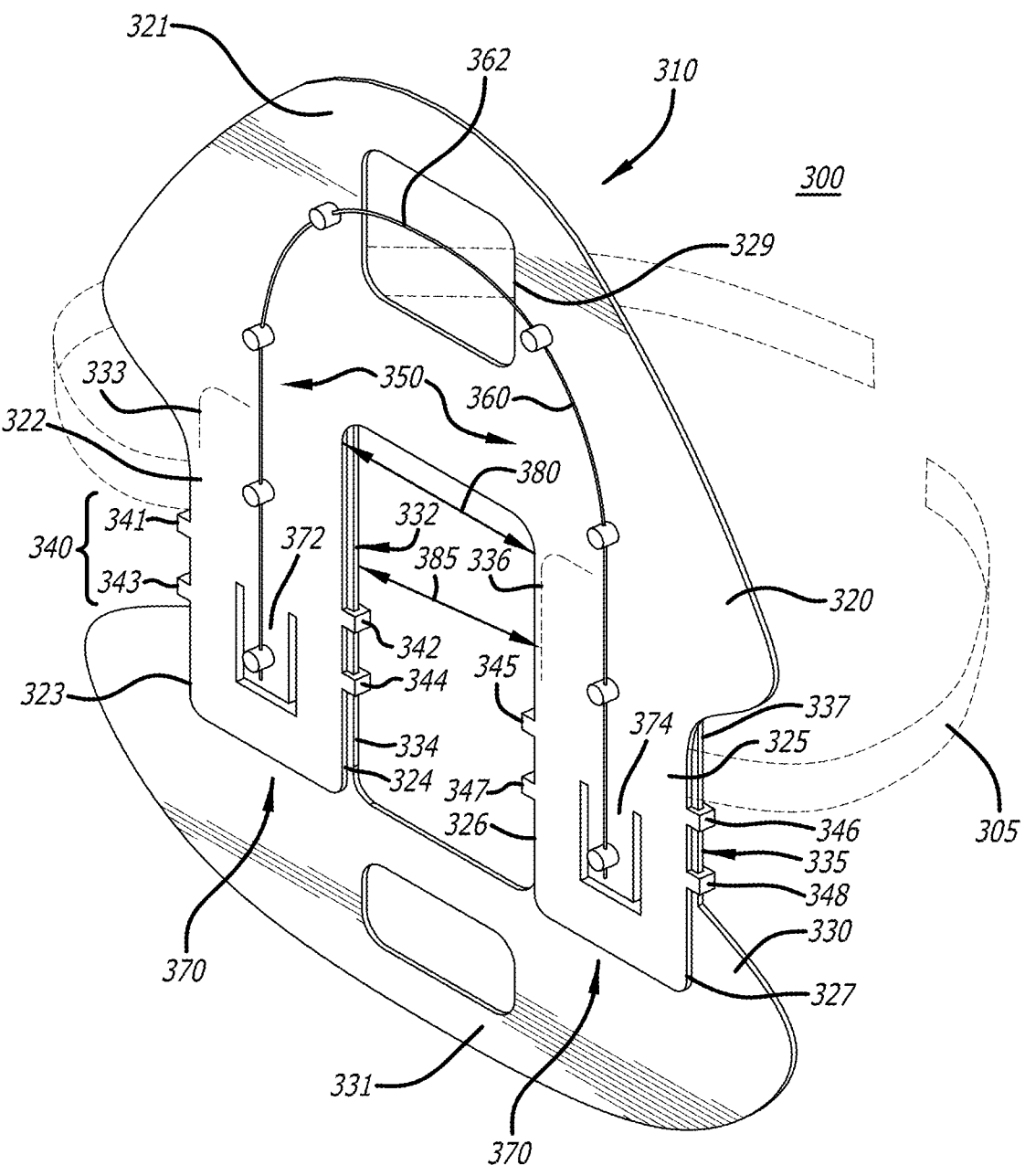
FIG. 3 is a second embodiment of an orthosis featuring a multi-panel, adjustable posterior frame along with height adjustment fasteners operating in cooperation with a fastener adjustment guide wire.

Referring to FIG. 3, a second embodiment of an orthosis 300 featuring an adjustable posterior frame 310, which includes multiple panels 320 and 330 that are slidably engaged and partially controlled by a fastener adjustment guide 360, is shown. A belt 305 may be attached to the posterior frame 310 to secure the orthosis 300 to the patient.

It is contemplated that the belt 305 may correspond to an LSO style belt so that, with the posterior frame 310, the orthosis operates as a TLSO.

Similar to FIG. 1, the posterior frame 310 includes (i) a first panel 320 featuring an upper area 321 and first pair of columns 322 and 325, a second panel 330 featuring a lower area 331 and a second pair of columns 332 and 335, a plurality of panel guide elements 340 (e.g., panel guide elements 341-348), and a fastening mechanism 350. Unlike the fastening mechanism 140 for the orthosis 10 of FIG. 1, the fastening mechanism 350 further includes the fastener adjustment guide 360 adapted to allow a clinician to partially disengage the first panel 320 from the second panel 330.

Herein, the panel guide elements 341-348 extend from the first panel 320 to engage with a plurality of edges of the second panel 330. As an illustrative example, the first panel 320 may be positioned posteriorly to the second panel 330, where a first set of guide elements 341 and 343 extend from a first edge 323 of a first column 322 of the first panel 320 to engage with a first edge 333 of a first column 332 of the second panel 330. A second set of guide elements 342 and 344 extend from a second edge 324 of the first column 322 of the first panel 320 to engage with a second edge 334 of the first column 332 of the second panel 330. Similarly, a third set of guide elements 345 and 347 extend from a first edge 326 of a second column 325 of the first panel 320 to engage with a first edge 336 of the second column 335 of the second panel 330, while a fourth set of guide elements 346 and 348 extend from a second edge 327 of the second column 325 of the first panel 320 to engage with a second edge 337 of the second column 335 of the second panel 330.

According to one embodiment of the disclosure, the panel guide elements 341-348 are configured to maintain positioning and a slidable connection between the first panel 320 and the second panel 330. This slidable connection allows the first panel 320 to be adjusted and secured to the second panel 330 using the fastening mechanism 350. Hence, the posterior frame 310 of the orthosis 300 may be adjusted to the patient's anatomy instead of a predetermined posterior back panel height.

According to one embodiment of the disclosure, the fastening mechanism 350 includes height adjustment fasteners 370, which may be deployed at one or more regions within columns 322 and 325 of the first panel 320. The height adjustment fasteners 370 may correspond to a number of different fastener types such as a flexible lift tabs as shown. Herein, both a first fastener 372 and a second fastener 374 are coupled to complementary locking members (not shown) implemented within the second panel 330 when the first and second fasteners 372 and 374 are placed into a locked state. The first and second fasteners 372 and 374 may be decoupled from the complementary locking members when the first and second fasteners 372 and 374 are placed into an unlocked state.

More specifically, the height adjustment fasteners 370 are mechanically coupled to the fastener adjustment guide 360. According to this embodiment, the fastener adjustment guide 360 may be formed as a wire that, in response to tensioning forces (e.g., upward, downward, inward, and/or outward) being placed thereon to activate the fastener adjustment guide 360 (e.g., pulling upward), the first and second fasteners 372 and 374 are placed into an unlocked state. When placed into an unlocked state, the fasteners 372 and 374 concurrently disengage from a set of locking members within the second panel 330.

Referring still to FIG. 3, the first panel 320 includes the upper area 321 with the first column 322 and the second column 325 extending downward (when worn) from the upper area 321. The upper area 321 is triangular-shaped as this portion of the adjustable posterior frame 100 may operate as a headrest for some patients or an upper back support for other patients. A first spacing 380 is provided between the first column 322 and the second column 325 of the first panel 320 while a second spacing 385 is provided between the first column 332 and the second column 335 of the second panel 330. The fastener adjustment guide (wire) 360 extends from the first fastener 372 (located towards a bottom portion of the first column 322 of the first panel 320) through the upper area 321 of the first panel 320 to the second fastener 374 (located towards a bottom portion of the second column 325 of the first panel 320). As shown, the fastener adjustment guide 360 is accessible along the first and second columns 322 and 325 as well as within the upper area 321. However, it is contemplated that the first panel 320 may be configured with a thickness to conceal most of the fastener adjustment guide 360 so that only a segment 362 of the fastener adjustment guide 360 is accessible through a slot 329 within the first panel 320.

Responsive to a tension being applied to the segment 362 of the fastener adjustment guide 360, the first and second fasteners 372 and 374 are laterally adjusted to disengage from their counterpart locking members within the second panel 330. This enables the first panel 320 to move vertically while maintaining its physical relationship with the second panel 330.

Figure 4A:
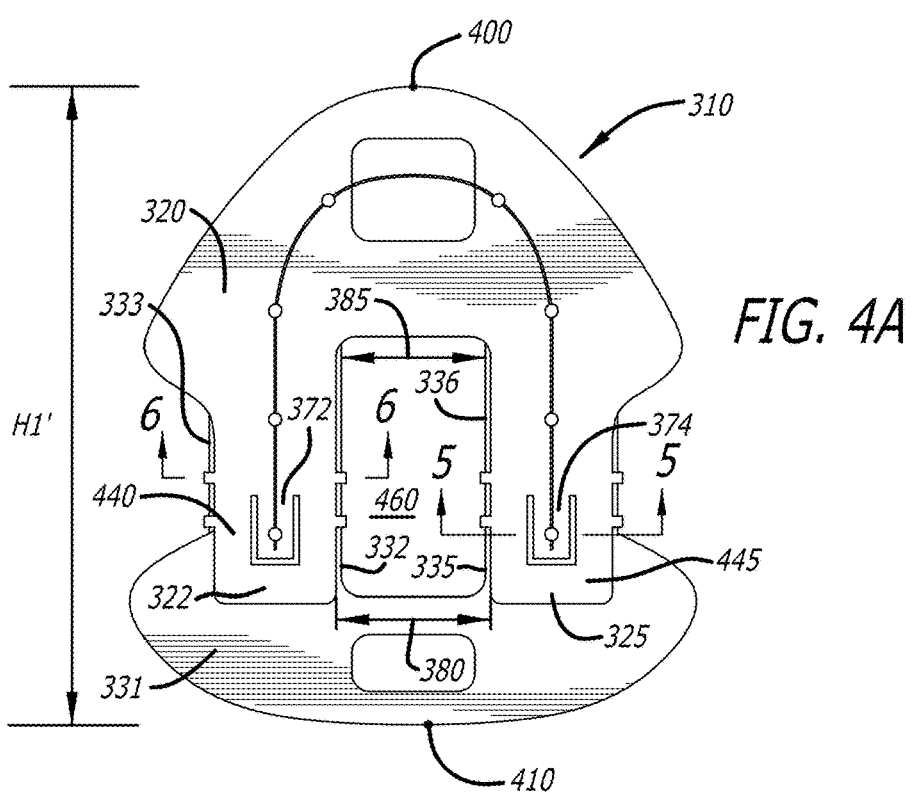
FIG. 4A is a perspective view of the multi-panel, adjustable posterior frame of FIG. 3 positioned in a first state of operation.
Figure 4B:
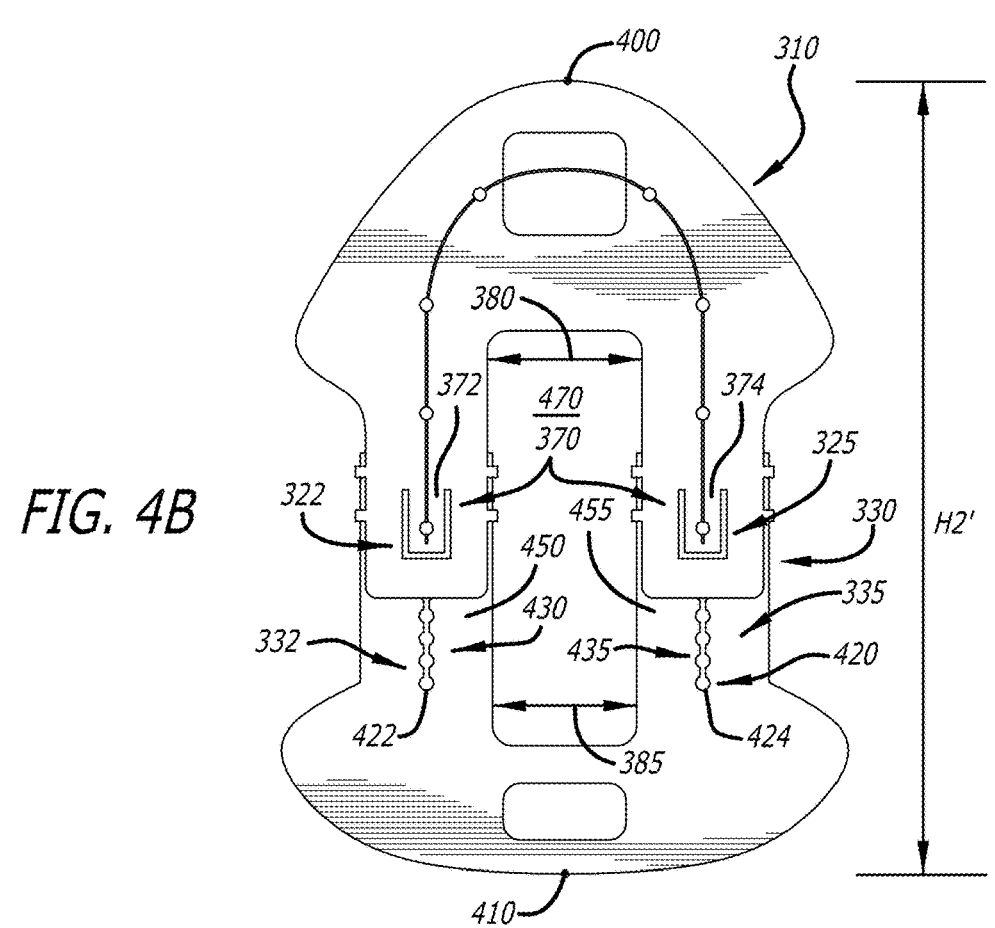
FIG. 4B is perspective view of the multi-panel, adjustable posterior frame of FIG. 3 positioned in a second state of operation.

Referring now to FIG. 4A, a perspective view of the adjustable posterior frame 310 of FIG. 3 positioned in a first state of operation is shown. Herein, portions of both the first and second columns 322 and 325 of the first panel 320 overlap the lower end 331 of the second panel 330. The first and second fasteners 372 and 374, which may correspond to flexible lift tabs for example, are inserted into and secured by a first set of locking members (e.g., lowest set of locking members 420 identified by a first locking member 422 of locking members 430 formed within the first column 332 of the second panel 330 and a first locking member 424 of locking members 435 formed within the second column 335 of the second panel 330 as shown in FIG. 4B. This setting places the adjustable posterior frame 310 into its smallest configuration.

More specifically, the height adjustment fasteners 372/374 are coupled to the first set of locking members 420 (interlocking apertures), where the posterior frame 310 is configured with a first height (H1') denoting a first vertical distance from an uppermost point 400 of the first panel 320 to a lowermost point 410 of the second panel 330.

As shown in both FIGS. 4A-4B, each of the height adjustment fasteners 370 (e.g., the first fastener 372 and/or the second fastener 374) is positioned at posterior surfaces 440 and 445 of the first pair of columns 322 and 325, respectively. Each of the first fastener 372 and/or the second fastener 374 includes a protrusion (not shown), which extends anteriorly from these fasteners 372 and 374 and beyond posterior surfaces 450 and 455 of the second pair of columns 330. These protrusions are sized to engage with a set of locking members within the second panel 330 as shown in FIGS. 5A-5B.

As further shown in FIGS. 4A-4B, the second panel 330 includes a lower area 331 and the second pair of columns 332 and 335 extending upward from the lower area 331 so as to overlay, from an anterior perspective, the first pair of columns 322 and 325. The spacing 380 between the first pair of columns 322 and 325 along with the spacing 385 between the second pair of columns 332 and 335 collectively create a rectangular window 460 to allow clinicians access to a patient's back, which is needed in follow-up visits after back surgery.

Referring now to FIG. 4B, a perspective view of the adjustable posterior frame 310 of FIG. 4A oriented in a second position is shown. Herein, the height adjustment fasteners 370 (e.g., fasteners 372/374) are coupled to the another set of locking members (interlocking apertures), where the posterior frame 310 is configured with a second height (H2') denoting a second vertical distance from the uppermost point 400 of the first panel 320 to a lowermost point 410 of the second panel 330. The second height (H2') is greater than the first height (H1'), as a difference in length is commensurate with a distance between the first set of locking members 420 to which the height adjustment fasteners 370 are coupled when placed in the first position and a second set of locking members (not shown) to which the height adjustment fasteners 370 are coupled when placed in the second position. A rectangular window 470 formed by the spacings 380 and 385 produce by the first pair of columns 322/325 and the second pair of columns 332/335 is larger in size than the rectangular window 460 when the adjustable posterior frame 310 is oriented in the first position. Similar to the height H2 of FIG. 2B, it is contemplated that the second height (H2') may be about 15½ inches.

Figure 5A:
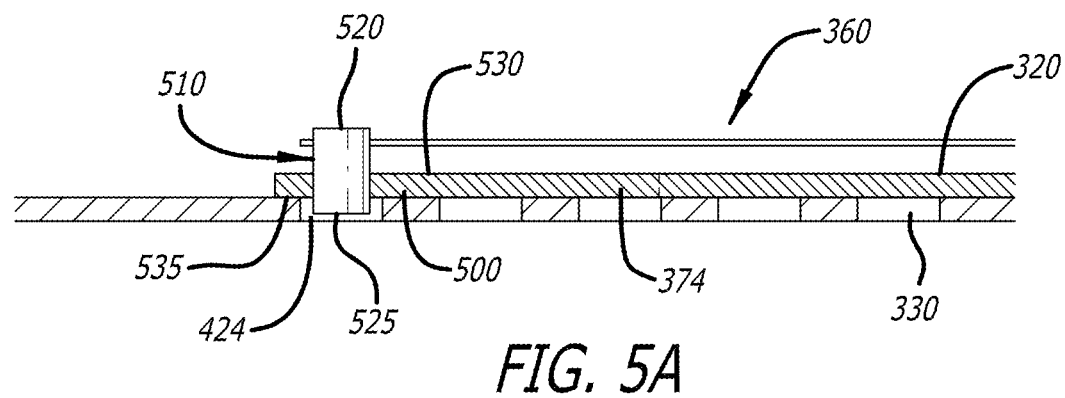
FIG. 5A is a cross-sectional view, along line 5-5 of FIG. 4A, of an embodiment of a height adjustment fastener managed by the fastener adjustment guide wire to place the height adjustment fastener into a locked state.
Figure 5B:
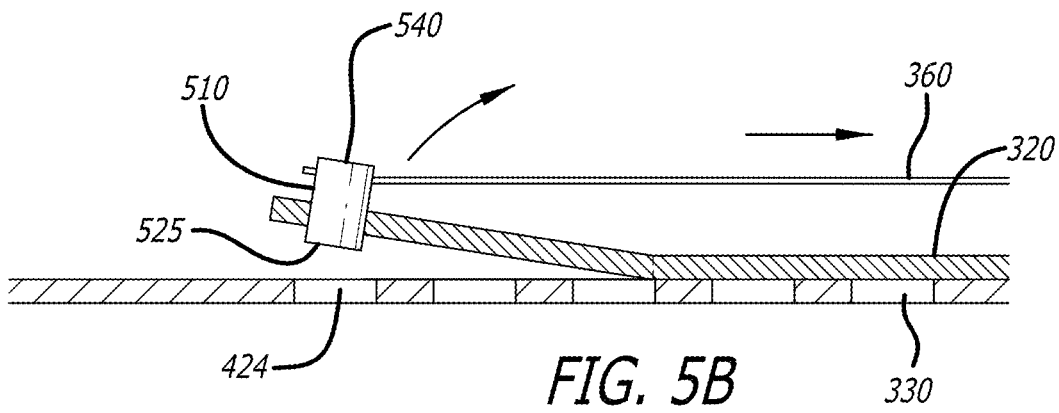
FIG. 5B is a cross-sectional view, along line 5-5 of FIG. 4A, of the height adjustment fastener of FIG. 5A placed into a locked state.

Referring now to FIGS. 5A-5B, cross-sectional views of an embodiment of the fastener adjustment guide 360 along line 5-5 of FIG. 4A operating to place the second height adjustment fastener 374 into a locked state (FIG. 5A) and an unlocked state (FIG. 5B) is shown. Herein, the fastener adjustment guide 360 performs independent or concurrent operations on both the first fastener 372 and the second fastener 374, albeit the operations of the fastener adjustment guide 360 on the second fastener 374 is represented herein. In fact, the adjustment guide 360 could be individually operated on each side.

As shown in FIG. 5A, according to one embodiment of the disclosure, the second fastener 374 features a base plate 500 and a first fastening element 510, which includes a first end portion 520 configured to extend from a top surface 530 of the base plate 500 and a second end portion 525 configured to extend from a bottom surface 535 of the base plate 500. The fastener adjustment guide 360 is coupled to the first end portion 520 of the first fastening element 510. When placed in a locked state, no tension is applied by the fastener adjustment guide 360 to cause movement of the first fastening element 510 away from the base plate 500. Hence, the second end portion 525 of the first fastening element 510 remains positioned within the locking member (aperture) 424 formed within the second panel 330.

As shown in FIG. 5B, the first fastening element 510 is placed in an unlocked state when tension 540 is applied to the fastener adjustment guide 360 to cause movement of the first fastening element 510 (and perhaps base plate 500) away from the second panel 330. Based on movement of the first fastening element 510, the second end portion 525 of the first fastening element 510 is extracted from the locking member (aperture) 424 formed within the second panel 330. As a result, the first panel 320 may be moved upward or downward based on the current positioning of the first fastening element 510 relative to the sets of locking members. For instance, if the second end portion 525 resides within a highest set of locking members, the first panel 320 may be moved downward to shorten the height. Similarly, where the second end portion 525 resides within a lowest set of locking members, such as locking member 424 as shown, the first panel 320 may be moved upward to increase the overall height of the adjustable posterior frame 310.

Figure 6:
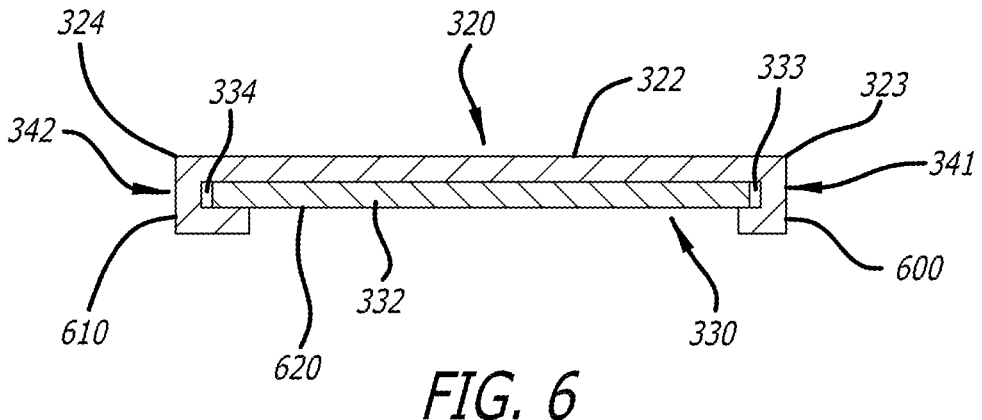
FIG. 6 is a cross-sectional view of an embodiment of portions of the first panel along line 6-6 of FIG. 4A, inclusive of the first and second panel guide elements.

Referring to FIG. 6, a cross-sectional view of an embodiment of portions of the first column 322 and the second column 332 along line 6-6 of FIG. 4A, inclusive of the first and second panel guide elements 341-342 is shown. Herein, the first and second panel guide elements 341-342 are configured to assist in retaining a substantially parallel orientation of and slidable engagement between the dual adjustable panels 320 and 330 of the posterior frame 310. Herein, the first panel guide element 341 includes a flange portion 600 that extends from the first edge 323 of the first column 322 of the first panel 320 to partially circumvent the first edge 333 of the first column 332 of the second panel 330. Similarly, the second panel guide element 342 includes a flange portion 610 that extends from the second edge 324 of the first column 322 of the first panel 320 to partially circumvent the second edge 334 of the first column 332 of the second panel 330. As a result, both the first and second panel guide elements 341 and 342 is positioned to rest adjacent to an anterior surface 620 of the first column 332 of the second panel 330. Hence, the substantial parallel orientation of the first and second panels 320 and 330 is retained during adjustment of the height of the posterior frame 310.

Figure 7:
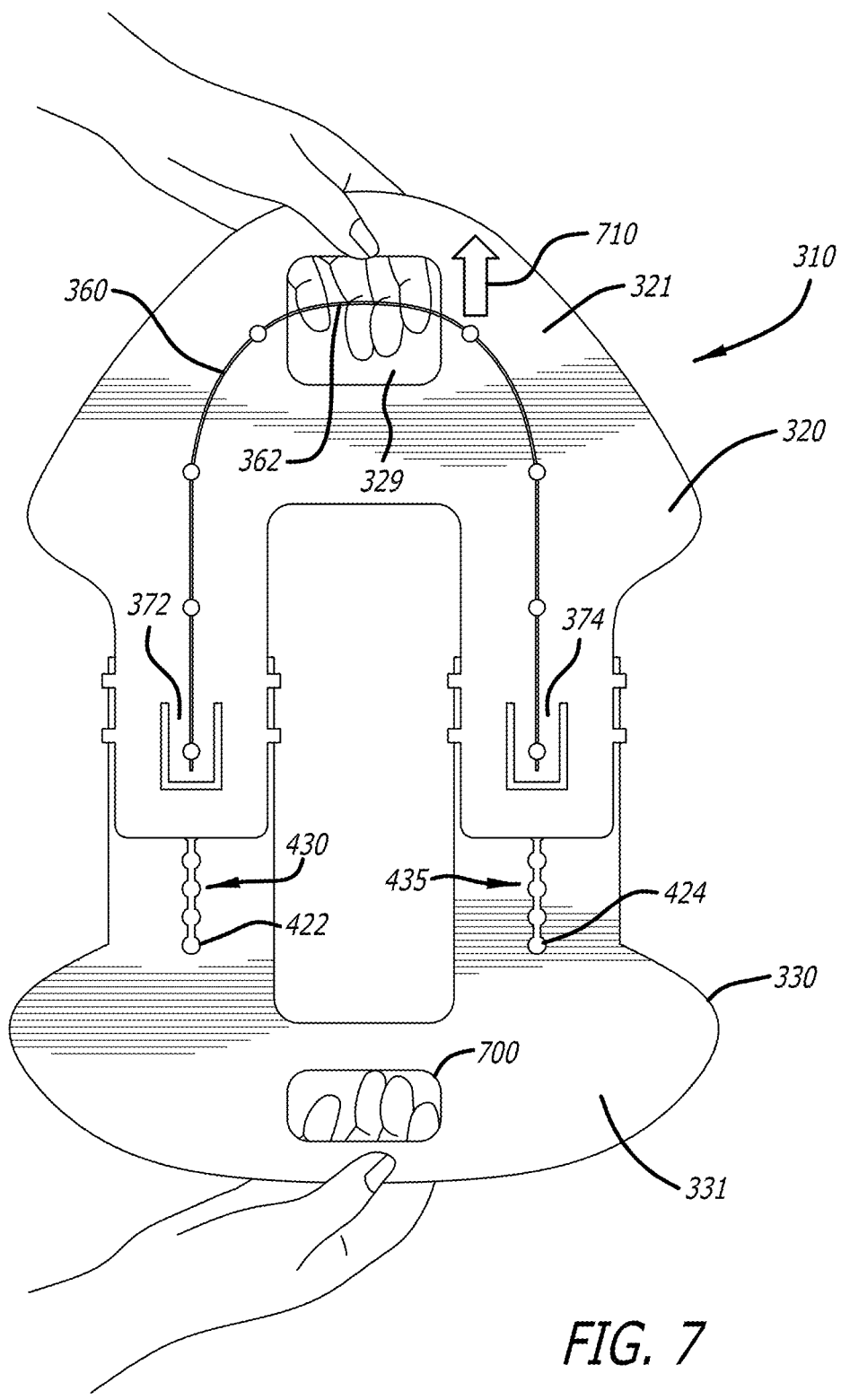
FIG. 7 is an exemplary embodiment of an adjustment process of the multi-panel, adjustable posterior frame of FIG. 3.

Referring now to FIG. 7, an exemplary embodiment of an adjustment process of the first and second panels 320 and 330 of the posterior frame 310 of FIG. 3 is shown. Herein, the upper area 321 of the first panel 320 includes the slot 329 and the lower area 331 of the second panel 330 includes a slot 700. Upon applying a tensioning force 710 to the segment 362 of the fastener adjustment guide 360, the first fastener 372 and the second fastener 374 of the first panel 320 would be able to be disengaged from corresponding locking members 422/424 within the second panel 330. After disengagement of the first and second fasteners 372 and 374 from the second panel 330, the user may extend the height of the posterior frame 310 by applying the upward force 710 (e.g., outwardly pulling the first panel 320 upward, pulling the first and second panels 320 and 330 in opposite directions, etc.). While upward forces 710 are continued to be applied to the fastener adjustment guide 360, the first and second fasteners 372 and 374 do not engage with locking members 430 and 435 formed within the second panel 330. However, when the upward forces 710 applied to the fastener adjustment guide 360 are discontinued, depending on a direction of movement of the first panel 320, the first and second fasteners 372 and 374 may engage with next locking member in the direction of movement.

It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A height adjustable back brace, comprising:
   a plurality of rear panels including a first rear panel and a second rear panel, wherein the first rear panel comprises at least a first fastener and the second rear panel comprises at least a first locking member configured to engage with the first fastener; and a fastener adjustment guide, wherein the first rear panel and the second rear panel are configured to move vertically relative to each other to position at least the first fastener to engage the first locking member at a first height, and wherein the fastener adjustment guide is a tensioning element communicatively coupled to at least the first fastener, wherein the tensioning element traverses over an upper region of the first rear panel and terminates at the first fastener, and upon applying a force to a segment of the fastener adjustment guide, the first fastener disengages from the first locking member.

2. The height adjustable back brace of claim 1, wherein the first fastener is a flexible tab having a protrusion.

3. The height adjustable back brace of claim 2, wherein the first locking member is a closed-ended slot sized and dimensioned to receive the protrusion.

4. The height adjustable back brace of claim 3, wherein the first locking member is an opening sized and dimensioned to receive the protrusion.

5. The height adjustable back brace of claim 1 wherein the first height is a first vertical distance from an uppermost point of the first rear panel to a lowermost point of the second rear panel.

6. An adjustable orthosis, comprising: a posterior frame including a first panel and a second panel, wherein the first panel comprises a first region, a second region, and a plurality of fasteners including at least a first fastener and a second fastener positioned as part of the second region and the second panel comprises a third region, a fourth region extending upward from the third region, and a plurality of locking members including at least a first locking member configured to engage with the first fastener and a second locking member configured to engage with the second fastener; and a fastener adjustment guide is a tensioning element communicatively coupled to at least the first fastener and the second fastener, wherein the tensioning element traverses over the first region of the first panel and terminates at both the first fastener and the second fastener, wherein upon applying a force to a segment of the tensioning element, the first fastener disengages from the first locking member and the second fastener disengages from the second locking member, wherein the first panel and the second panel are configured to move relative to each other to position the first fastener to engage (1) the first locking member at a first size or (2) the second locking member as a second size.

7. The adjustable orthosis of claim 6, wherein the first fastener is a first fastening device and the first locking member is a second fastening device.

8. The adjustable orthosis of claim 7, wherein the second region including a first plurality of columns including a first column and a second columns, the first column forms a first portion of the first panel and the second column forms a second portion of the first panel.

9. The adjustable orthosis of claim 8, wherein the plurality of locking members comprises (i) the first locking member and a third locking member positioned linearly from the first locking member and (ii) the second locking member and a fourth locking member positioned linearly from the second locking member,
   wherein the second fastener is configured to engage with either (i) the second locking member when the first fastener engages with the first locking member or (ii)

the fourth locking member when the first fastener engages with the third locking member.

10. The adjustable orthosis of claim 6, wherein the first fastener is a flexible tab having a protrusion.

11. The adjustable orthosis of claim 10, wherein one or more of the first locking member and the second locking member is an opening sized and dimensioned to receive the protrusion.

12. The adjustable orthosis of claim 6, wherein the tensioning element operating as the fastener adjustment guide is a wire.

13. The adjustable orthosis of claim 6, wherein the first size corresponds to a first height, the second size corresponds to a second height greater than the first height, and the first panel and the second panel are configured to move vertically relative to each other.

14. A height adjustable posterior frame, comprising: a first panel including an upper region, a first panel region extending from the upper region, and a first set of fasteners including at least a first fastener and a second fastener; a second panel including a lower region, a second panel region extending from the lower region, a first set of locking members to engage with the first fastener and a second set of locking members to engage with the second fastener, wherein the first panel is configured to move vertically relative to the second panel to position the first fastener to engage with one of the first set of locking members and the second fastener to engage with one of the second set of locking members; and a fastener adjustment guide is a tensioning element communicatively coupled to at least the first fastener and the second fastener, wherein the tensioning element traverses over the upper region of the first panel and terminates at both the first fastener and the second fastener, wherein, upon activation of the fastener adjustment guide by applying a force to a segment of the tensioning element, the first fastener is configured to disengage from one of the first set of locking members and the second fastener is configured to disengage from one of the second set of locking members to allow the first panel to be adjusted from a first height associated with the first set of locking members to a second height associated with the second set of locking members.

15. The height adjustable posterior frame of claim 14, wherein the first fastener is a flexible tab having a protrusion and a first locking member of the first set of locking members is an opening sized and dimensioned to receive the protrusion.

16. The height adjustable posterior frame of claim 14, wherein the first fastener is a first fastening device and a first locking member of the first set of locking members is a second fastening device.

17. The height adjustable posterior frame of claim 14, wherein the fastener adjustment guide is a wire.

18. The height adjustable posterior frame of claim 14, wherein the first panel and the second panel are configured to move vertically relative to each other to set the posterior frame at a first size corresponding to the first height or a second size corresponds to the second height, wherein the second height is greater than the first height.

19. The height adjustable posterior frame of claim 14, wherein the first panel and the second panel are coupled to a belt configured for placement around a torso of a patient.

* * * * *